United States Patent [19]

Uram

[11] Patent Number: 5,323,766
[45] Date of Patent: * Jun. 28, 1994

[54] ILLUMINATING ENDO-PHOTOCOAGULATION PROBE

[75] Inventor: Martin Uram, Little Silver, N.J.

[73] Assignee: Endo Optiks Corporation, Little Silver, N.J.

[*] Notice: The portion of the term of this patent subsequent to Jun. 16, 2009 has been disclaimed.

[21] Appl. No.: 893,700

[22] Filed: Jun. 5, 1992

Related U.S. Application Data

[63] Continuation-in-part of Ser. No. 737,054, Jul. 29, 1991, Pat. No. 5,121,740, which is a continuation-in-part of Ser. No. 696,117, May 6, 1991, abandoned.

[51] Int. Cl.$^5$ .................. A61B 1/06; A61B 17/32
[52] U.S. Cl. .................................. 128/6; 128/11
[58] Field of Search ...................... 128/4, 6, 11

[56] References Cited

U.S. PATENT DOCUMENTS

| | | | |
|---|---|---|---|
| 3,858,577 | 1/1975 | Bass | 128/6 |
| 4,072,147 | 2/1978 | Hett | 128/6 |
| 4,207,874 | 6/1980 | Choy | 128/6 |
| 4,448,188 | 5/1984 | Loeb | 128/6 |
| 4,589,404 | 5/1986 | Barath | 128/6 |
| 4,604,992 | 8/1986 | Sato | 128/6 |
| 4,607,622 | 8/1986 | Fritch et al. | 128/6 |
| 4,697,210 | 9/1987 | Toyota et al. | 128/6 |
| 4,700,694 | 10/1987 | Shishido | 128/6 |
| 4,788,967 | 12/1988 | Ueda | 128/6 |
| 4,790,295 | 12/1988 | Tashiro | 128/6 |
| 4,834,070 | 5/1989 | Saitou | 128/6 |
| 4,896,941 | 1/1990 | Hayashi et al. | 128/6 |
| 4,928,695 | 5/1990 | Goldman et al. | 128/6 |
| 4,984,563 | 1/1991 | Renaud | 128/6 |
| 5,121,740 | 6/1992 | Uram | 128/6 |

Primary Examiner—Paul J. Hirsch
Attorney, Agent, or Firm—McAulay Fisher Nissen Goldberg & Kiel

[57] ABSTRACT

A surgical endo-probe particularly adapted for use in ophthalmological surgery includes a probe connected distally of a hand piece. Within the probe, there are at least two optical fibers. The first optical fiber constitute an illumination zone for illuminating the tissue to be operated on. A laser fiber provides pulses of laser energy to the tissue illuminated by the illumination fibers. The illumination zone can be a single fiber or a plurality of fibers.

4 Claims, 1 Drawing Sheet

ILLUMINATING ENDO-PHOTOCOAGULATION PROBE

REFERENCE TO RELATED APPLICATIONS

This application is a continuation-in-part of applicant's patent application Ser. No. 07/737,054 filed on Jul. 29, 1991 now U.S. Pat. No. 5,121,740 which is a continuation-in-part of applicant's patent application Ser. No. 07/696,117 filed on May 6, 1991, abandoned, both entitled: Laser Video Endoscope.

This invention relates in general to a small diameter endo-probe used for medical purposes and more particularly to one in which illumination, and laser operating functions are performed within a single small diameter endo-probe.

The endo-probe of this invention is designed particularly for use in certain ophthalmological operations and thus the disclosure herein will relate to such an embodiment.

It is known to apply laser energy, and other types of energy, both directly and indirectly to various parts of the eye in order to effect surgery. For example, laser energy has been used for operations involving repairs of retinal tears, repairing retinal detachment, for ablating the retina in treating proliferative retinopathies and also for the destruction of focal retinal or choroidal lesions.

These operations are normally made by a surgeon viewing through an operating microscope while holding a laser energy probe in one hand and a light pipe in another hand. The typical operating procedure is one where the surgeon has to insert and remove different instruments in sequence. The surgeon may have to insert a laser instrument and then remove it so that he can then use a cutting instrument by inserting and removing it and then use an aspirating instrument by inserting and removing it. This insertion and removal of various instruments increases trauma, increases the risk of error and takes time.

It is an important purpose of this invention to provide an endo-probe that provides laser energy which will permit a simplification in the operation by reducing the amount of insertion and withdrawal of instrument thus decreasing trauma and the time of the operation; all to serve the more ultimate object of patient safety and comfort.

BRIEF DESCRIPTION

In brief, this invention involves a fiber optic endo-probe supported by a handpiece. The hand piece is connected through a relatively long flexible lead to a laser energy source and a source of illumination. The flexible lead, hand piece and probe all contain a laser optical fiber and an optical fiber illumination zone.

The laser fiber is a monofilament fiber that provides the required pulses of laser energy to effect operation. In one embodiment, it has a diameter of approximately 0.25 mm.

Light transmitted down the illumination fiber zone emerges at the distal end of the probe to provide illumination at the area of operation. The area illuminated is viewed by the surgeon in a known standard mode employing an operating microscope.

With the image in view and the endo-probe in position, the surgeon can then control the transmission of laser energy, typically pulses of laser energy, through the monofilament laser fiber to the zone of the operation. Because the probe combines the delivery of laser energy and illumination, the surgeon has a free hand with which to separately insert and manipulate other instruments such as an aspirating instrument or a cutting instrument. Thus by providing this dual function instrument, the purposes of this invention are achieved.

DESCRIPTION OF THE PREFERRED EMBODIMENTS

Figure 1:
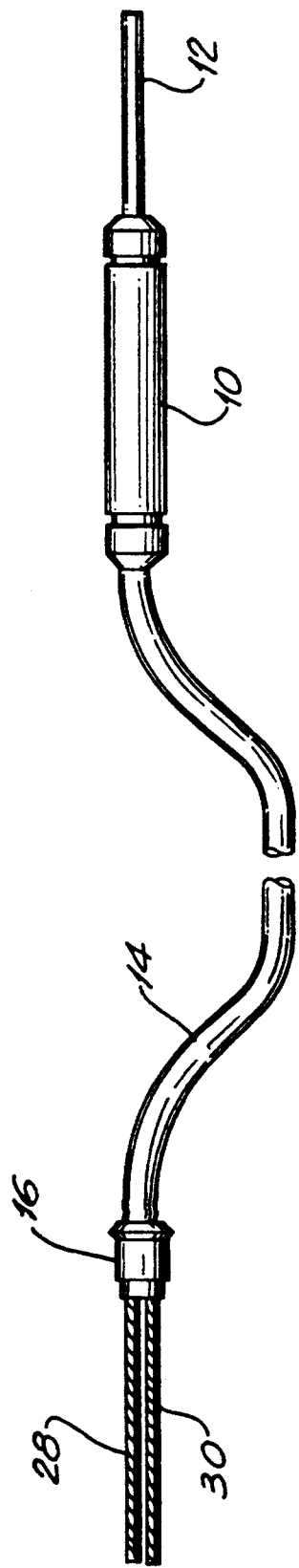
FIG. 1 is a mechanical schematic longitudinal view of a device embodying this invention.

As shown in the FIGS., the endo-probe of this invention has a hand piece 10 and a probe 12, which are connected through a flexible cable 14 to a connector 16.

Within the probe 12, the hand piece 10 and the first flexible cable 14 there is deployed two separate sets of optical fibers that perform two separate functions. These are shown in the cross-sectional view of FIG. 2. The cross-sectional view is taken at the tip of the probe 12. Within the probe 12 there is a monofilament laser fiber 22 and an illumination zone 26. The laser fiber 22 is a monofilament optical fiber that delivers the laser energy at the tip of the probe 12 for performing operations. The illumination zone 26 carries illumination toward the distal end of the probe 12.

In operation, light is transmitted down the illumination zone 26 to emerge at the distal end of the probe 12 to provide illumination at the area of operation. The image of at least part of the area illuminated is viewed using a known operating microscope. With the area to be operated on illuminated and the probe 12 in position, the surgeon can then control the transmission of the laser energy (usually pulses of laser energy) through the laser fiber 22 to the illuminated zone.

At the juncture 16, these two sets of fibers 22 and 26 are separated and carried in cables 28, 30 to be appropriately connected to a source of laser energy for the optical fiber set 22 and to a source of light for the set of fibers that constitute the illumination zone 26.

Figure 2:
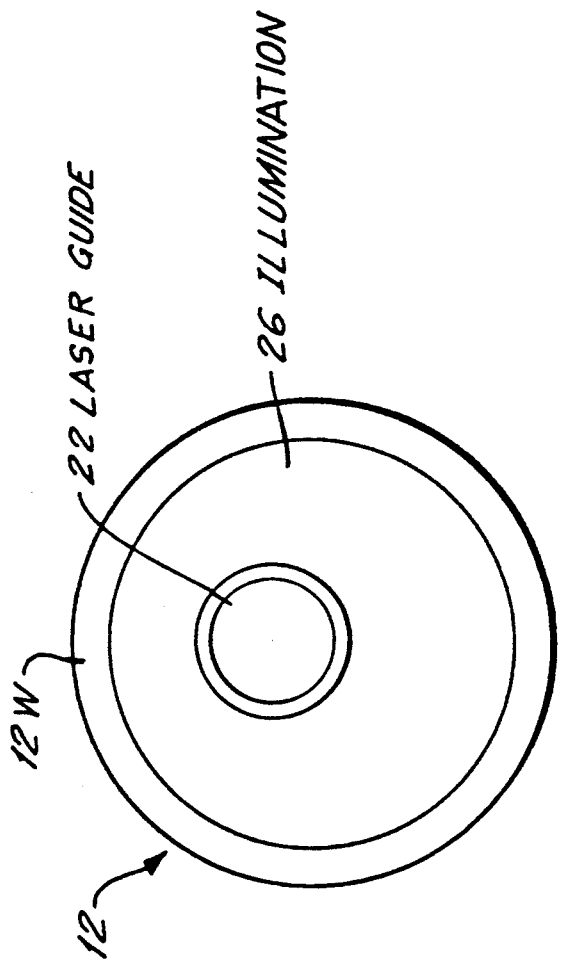
FIG. 2 is a cross-sectional view at the tip of the probe 12 showing the laser fiber 22 within a multi-filament illumination zone 26 that fills the probe.

In the FIG. 2 embodiment, one representation has been manufactured and tested as a stainless steel probe 12 with an outer diameter of approximately 950 microns, an inner diameter of approximately 800 microns, and a wall 12w thickness of approximately 125 microns. The laser guide 22 is a 250 micron quartz monofilament fiber clad with silica to provide a 250 micron light pipe. The illumination zone 26 has about five hundred optical fibers with each fiber having a diameter of approximately thirty microns including cladding. These optical fibers are strung randomly down the length of the instrument and are potted into place only at the tip of the operating probe 12.

Positioning the laser guide 22 in the center of the illumination zone 26 means that the laser energy can be delivered to the center of the tissue being illuminated.

The probe 12 is thirty mm long, the handpiece 10 is 40 mm long and the cable 14 is 1.5 meters long.

As is known in the art, the particular laser guide optical material is selected as a function of the frequency of the laser light pulses which are to be transmitted by the guide. In the embodiment tested, the laser used is a diode laser composed of gallium-aluminum-arsenide semi-conducting crystals to provide a wave length of about 810 nano meters (in the range of 780 nm to 850 nm).

The joint 16 where the components 22, 26 of the interior of the probe 12 are brought together is fabricated by standard techniques known in the art including the use of heat shrink tubing at the connector.

The embodiment illustrated has the straight probe 12 shown. Applicant believes there may be advantage in a slight curvature to the probe 12 so that the tip of the probe is displaced two to three mm from the axis. This might provide advantage in use of more readily clearing the lens of the eye.

It should be noted that the combination of the illumination zone and laser guide within a single probe provides a particularly compact probe for performing these functions. Because the probe 12 is compact and circular in cross section, a minimal incision of the sclera is required while meeting the objectives of this invention to free one hand of the surgeon and reduce the number of times instruments have to be inserted and withdrawn during an operation.

What I claim is:

1. In a surgical endo-probe having a hand piece, a probe attached to one end of the hand piece and a connecting cable attached to the other end of the hand piece, the probe improvement comprising:

a tubular support wall, an illuminating zone comprising a plurality of optical fibers extending longitudinally within said support wall, the hand piece and the connecting cable, said illuminating zone having an outer periphery that matches the inner periphery of said tubular support wall, an optical laser guide comprising at lest one longitudinally extending optical fiber, said laser guide being positioned within said illumination zone, the sole elements within said tubular support wall being said illumination zone and said laser guide, whereby light applied through said illumination zone will illuminate any tissue at the distal end of the probe which is to be operated on by the laser energy delivered through said laser guide.

2. The endo-probe improvement of claim 1 wherein: said optical laser guide is a monofilament laser fiber.

3. The endo-probe of claim 1 wherein said laser guide is substantially centered in said illumination zone.

4. The endo-probe of claim 2 wherein said laser guide is substantially centered in said illumination zone.

* * * * *